| United States Patent [19] | [11] | 4,072,045 |
|---|---|---|
| Kopito | [45] | Feb. 7, 1978 |

[54] VISCOMETER FOR INDICATING RHEOLOGICAL PROPERTIES OF FLUIDS HAVING HIGH AND LOW VISCOSITY COMPONENTS

[75] Inventor: Louis Kopito, Brookline, Mass.

[73] Assignee: Ovutime, Inc., Brookline, Mass.

[21] Appl. No.: 722,229

[22] Filed: Sept. 10, 1976

[51] Int. Cl.² ............................................ G01N 33/16
[52] U.S. Cl. .......................................................... 73/54
[58] Field of Search ........................... 73/54, 64.4, 53; 128/2 W; 23/230 B

[56] References Cited

U.S. PATENT DOCUMENTS

| 3,926,037 | 12/1975 | Kopito et al. | 73/53 |
| 3,979,945 | 9/1976 | Kopito et al. | 73/54 |
| 3,982,423 | 9/1976 | Schuster | 73/54 |
| 4,002,056 | 1/1977 | Kopito et al. | 73/64.4 |

*Primary Examiner*—Richard C. Queisser
*Assistant Examiner*—Joseph W. Roskos
*Attorney, Agent, or Firm*—Morse, Altman, Oates & Bello

[57] ABSTRACT

A fluid having high and low viscosity components is introduced into the test region between a pair of bearing members which are biased for relative motion and which are characterized by at least one porous bearing surface. The low viscosity component is absorbed by the porous bearing surface. The high viscosity component remains in the test region to establish characteristics which are indicated by the relative motion between the bearing members. The rheological properties of the high viscosity component are a function of these characteristics.

16 Claims, 6 Drawing Figures

VISCOMETER FOR INDICATING RHEOLOGICAL PROPERTIES OF FLUIDS HAVING HIGH AND LOW VISCOSITY COMPONENTS

RELATED APPLICATIONS

The present application is related to copending application Ser. No. 523,047, filed Nov. 12, 1975, now U.S. Pat. No. 3,982,423, issued Sept. 28, 1976 which is a continuation-in-part of application Ser. No. 462,298, filed Apr. 19, 1974, which in turn is a continuation-in-part of application Ser. No. 433,767, filed Jan. 16, 1974, which in turn is a continuation-in-part of application Ser. No. 300,187, filed Oct. 24, 1972. The present application also is related to application Ser. No. 629,700, filed Nov. 7, 1975, now U.S. Pat. No. 4,013,066, issued Mar. 22, 1977, which is a continuation-in-part of earlier application Ser. No. 472,611, filed May 23, 1974, which in turn is a continuation-in-part of aforesaid application Ser. No. 300,187, filed Oct. 24, 1972. The present invention also is related to copending application Ser. No. 637,830, filed Dec. 4, 1975, now U.S. Pat. No. 4,002,056, issued Jan. 11, 1977, which is a continuation-in-part of application Ser. No. 558,247, filed Mar. 14, 1975, now U.S. Pat. No. 3,926,037 issued Dec. 16, 1975. The present application also is related to copending application Ser. No. 573,348, filed Apr. 30, 1975 now U.S. Pat. No. 3,979,945, issued Sept. 14, 1976. All of the foregoing applications and patents have a common assignee.

BACKGROUND OF THE INVENTION

1. Field of the Invention

The present invention relates to processes and devices for determining the rheological properties of fluids and, more particularly, to the estimation of differential rheological properties of heterogeneous fluids, particularly biological fluids such as saliva, ejaculates, cervical mucus and blood. Such fluids usually are composed of several liquid fractions of different chemical compositions, molecular weights and rheological properties.

2. The Prior Art

The determination of rheological properties of such heterogeneous fluids has been difficult because: (1) random structural variations from sample to sample complicate efforts to obtain reproducible values; (2) collection and testing of a sample can cause significant changes in its visco-elastic structure; (3) conditions in the test instrument are different from conditions in-vivo or in-situ; (4) particular measurements do not necessarily indicate particular visco-elastic structures; and (5) comparative standards of known visco-elastic structures generally are lacking. In particular, present on-the-spot testing techniques are inadequate.

SUMMARY OF THE INVENTION

The primary object of the present invention is to provide processes and devices, for testing fluids having high and low viscosity components, characterized by disposing a sample of such fluid in a test region between a pair of bearing members which are biased for relative motion and which are characterized by at least one porous bearing surface. Certain of the low viscosity components are absorbed by the porous bearing surface. Certain of the high viscosity components remain in the test region to establish characteristics, which are indicated by the relative motion between the bearing members. The rheological properties of these high viscosity components are a function of these characteristics. In one embodiment, the bearing members are cylindrical and one of the bearing members is provided with a port through which a predetermined amount of sample fluid can be introduced into the test region between the bearing surfaces under standardized shear conditions. In another embodiment, the bearing members are reciprocable, being provided with discrete parallel ridges or flutes, the outermost portions of which define ridge lines, the ridges of one bearing member being crossed with respect to the ridges of the other, the test region between the bearing surfaces being a tear region. The present invention takes advantage of the fact that, from a practical (rather than a purely scientific) standpoint, it frequently is not necessary to measure exact rheological values of some fluids in order to yield technically significant information.

Other objects of the present invention in part will be obvious and in part will appear hereinafter.

The invention accordingly comprises the products and processes, together with their parts, steps and inter-relationships, which are exemplified in the present disclosure, the scope of which will be indicated in the appended claims.

BRIEF DESCRIPTION OF THE DRAWINGS

For a fuller understanding of the nature and scope of the present invention, reference is made to the following detailed specification, which is to be taken in connection with the accompanying drawings wherein.

DETAILED DESCRIPTION OF THE EMBODIMENT OF FIGS. 1, 2 AND 3

Figure 1:
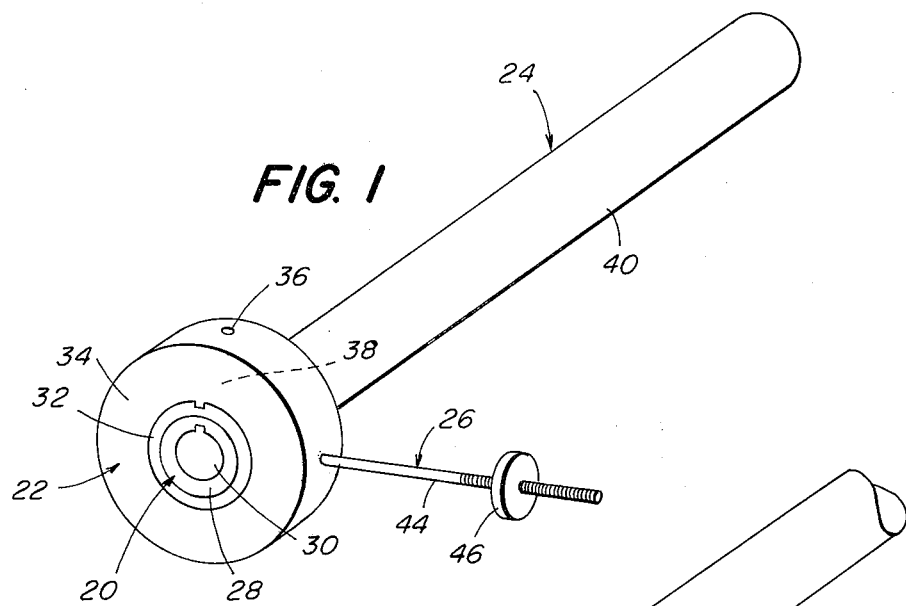
FIG. 1 is a perspective view of a product embodying the present invention.
Figure 2:
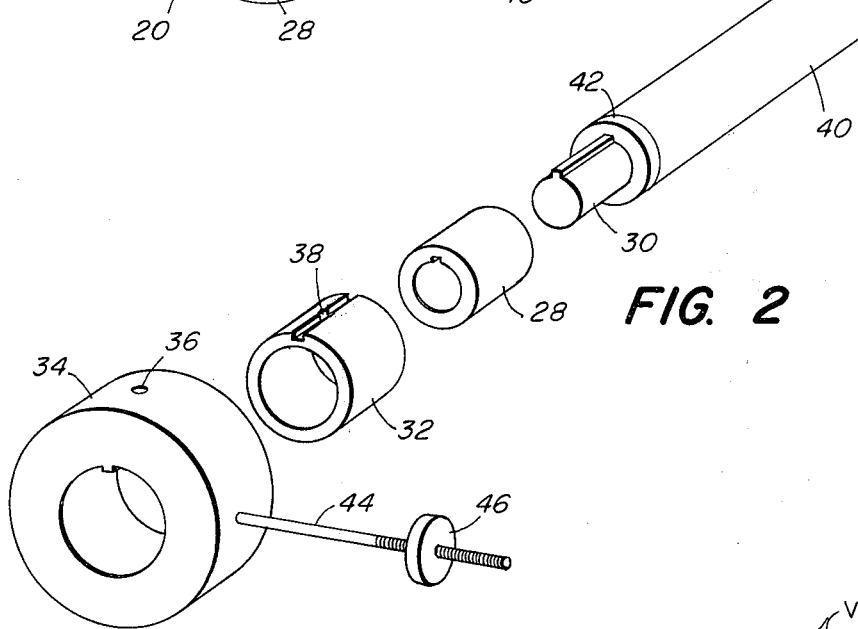
FIG. 2 is a perspective, exploded view of the components of the product of FIG. 1.

One embodiment of the present invention, as shown in FIGS. 1 and 2, comprises an inner bearing assemblage 20 and an outer bearing assemblage 22, between which a specimen is tested in accordance with the present invention; a support assemblage 24 for carrying inner bearing assemblage 20; and a bias assemblage 26 for causing or not causing relative motion between the inner and outer bearing assemblages during testing of a fluid therebetween As shown, inner bearing assemblage 20 includes an inner bearing ring 28 having an outer cylindrical bearing surface, which is porous in accordance with the present invention. Bearing ring 28 has an inner cylindrical surface with a keyway. Bearing assemblage 22 also includes a cylindrical mount 30 that has an outer cylindrical surface with a key. Ring 28 and mount 30 snugly mate with each other so that they can be fitted together manually, retained in mated condition frictionally, or separated from each other manually as desired.

As shown, outer bearing assemblage 22 includes an outer bearing ring 32 having an inner bearing surface which is porous in accordance with the present invention. Bearing ring 32 has an outer cylindrical surface with a keyway. Bearing assemblage 22 also includes an annular mount 34 that has an inner cylindrical surface with a key. Ring 32 and mount 34 mate with each other so that they can be fitted together manually, retained in mated condition frictionally, or separated from each other manually as desired.

Bearing mount 34 has a port 36 extending from its outer to its inner surface and bearing ring 32 has a port 38 extending from its outer to its inner surface. When bearing mount 34 and bearing ring 32 are mated, ports 36 and 38 are aligned and constitute an orifice through which a metered sample of fluid can be introduced by a syringe or the like into the shear region between the inner and outer bearing surfaces. Support assemblage 24 is in the form of horizontal rod 40 that, as shown, is adapted to be manually held. The outer diameter of rod 40 and the outer diameter of bearing ring 28 are the same so as to establish a continuous cylindrical surface. On rod 40 is a marker 42, which indicates the desired axial location of outer bearing assemblage 22 on inner bearing assemblage 20. Bias assemblage 26 includes a threaded shaft 44 that extends radially from annular bearing mount 22 and a threaded nut 46 that is turned onto shaft 44 to an adjusted position at which selected bias is achieved.

In accordance with the present invention, at least one and preferably both of the bearing surfaces of ring 28 and ring 32 are predeterminedly porous, being characterized by sufficient capillarity to absorb water and other aqueous, substantially Newtonian free-flowing fluids. Preferably the axial length of outer ring 32 is sufficiently short, i.e. between 0.3 and 5 centimeters, and the radial distance between the inner and outer bearing surfaces is sufficiently small, i.e. between 0.0001 and 0.050 millimeters, so that a small sample of the fluid, i.e. 1 to 1000 microliters, will fill the shear region. Preferably, each of the two bearing surfaces should have an area of at least 250 millimeters so as to ensure that the absorptive capacity of the surfaces will not be saturated. Preferably the pore diameter should average in the range from 0.1 to 500 microns and the depth of the porous layer underlying the porous surface should be in excess of 1 micron, ranging normally up to 200 microns. Preferably the outside diameter of inner ring 28 ranges from 0.3 to 2.0 centimeters. In various forms, the porous bearing surfaces are provided by fired ceramic materials, etched vitrious materials (particularly glasses), sintered powder metallurgical composites, and etched metals and alloys. A particularly satisfactory material is produced by etching the copper out of aluminum bronze by an acid, particularly sulphuric acid.

Figure 3:
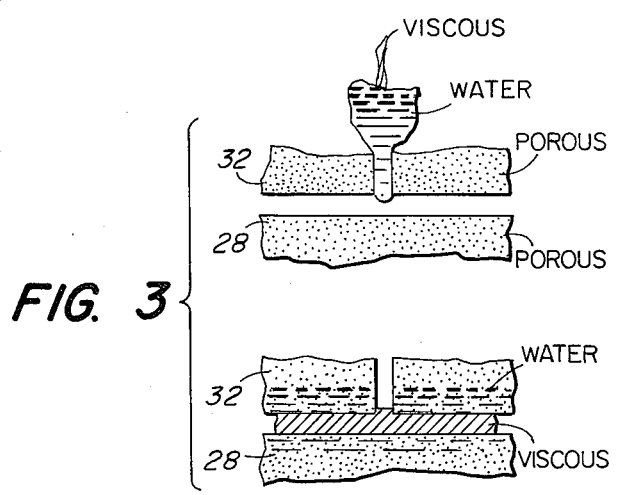
FIG. 3 is a flow illustration, exaggerated for emphasis, of the steps of a process of the present invention.

OPERATION OF THE EMBODIMENT OF FIGS. 1, 2 and 3

The following non-limiting examples further illustrate the present invention. In each of these examples the axial length of outer ring 32 is approximately 2 centimeters, the radial distance between the inner and outer bearing surfaces is approximately 0.01 millimeter, the bearing surfaces each has areas of approximately 500 millimeters, the average pore diameter is approximately 100 microns, the depth of each of the porous layers is approximately 100 microns. The process of the present invention contemplates indicating visco-elastic changes in biological fluids resulting from pathological conditions, drug usage, the menstrual cycle, etc.

EXAMPLE I

In the case of obstructive pulmonary diseases such as bronchitis, cystic fibrosis and emphysema, thick viscous discharges are expectorated. The obstructive fractions are intermixed with saliva, pulmonary surfactants, bacteria, water, electroytes and other components. There are no "pure samples" and no two consecutive specimens are alike since they may originate from the bronchi or alveoli in different locations in the lungs involving regions that may be more or less seriously involved. Certain drugs known as mucolytic agents are used to liquefy the tenacious viscous fractions although their efficacy is difficult to measure. In accordance with the present invention, testing a sample of such an expectorated discharge involves inserting it into the shear region between the two porous bearing surfaces of the test instrument, absorbing the more fluid components into the bearing surfaces and biasing the bearing surfaces for relative movement in order to determine the lubricity of the residue.

EXAMPLE II

The present invention is useful in determining the phase of the menstrual cycle and, particularly, to indicating the rheological properties of bodily mucus, particularly cervical mucus and/or oral mucus, in order to predict the inception and to indicate the presence of ovulation. The present invention thus is concerned with conception control. It has been found that mucus samples from the vaginal and oral cavities undergo distinct in-phase rheological changes during the menstrual cycle. Although the changes in the cervical mucus are much more noticeable than the changes in the oral mucus, both changes are readily determinable. During the immediate pre-ovulatory phase, for a period of 1 to 3 days under estrogen domination, the mucus is profuse and watery. During the post-ovulatory phase, under progestation, the mucus becomes less abundant and more viscous. In healthy women with normal menstrual cycles, as is well documented in the medical literature, ovulation usually occurs between the 12th and 14th day prior to the next menstrual period (and not after the preceding period). Specifically, cervical mucus is most hydrated at the time of ovulation, containing 97 to 98% water, and is relatively dehydrated at other times, containing only 80 to 90% water. The solid residue after desiccation may range from 2% during ovulation to 20% at other times, a 10 fold increase. In accordance with the present invention, testing a sample of cervical mucus involves inserting it into the shear region between the two porous bearing surfaces of the test instrument, absorbing the watery fluid components into the bearing surfaces and biasing the bearing surfaces for relative motion in order to determine the lubricity of the residue.

In each of the foregoing examples, testing of the residue involved establishing a predetermined torque, which either causes rotation of the outer bearing member or does not cause rotation of the outer bearing member as an indication of lubricity.

DETAILED DESCRIPTION OF THE EMBODIMENT OF FIGS. 4, 5 AND 6

Figure 6:
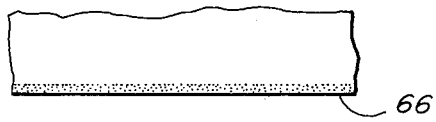
FIG. 6 is an exaggerated cross sectional view of the components illustrated in FIG. 5.
Figure 6:
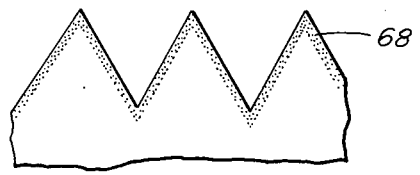
Figure 5:
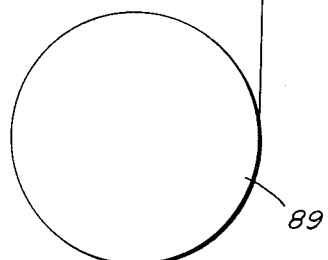
FIG. 5 is an exaggerated perspective view, illustrating certain features of the present invention.
Figure 5:
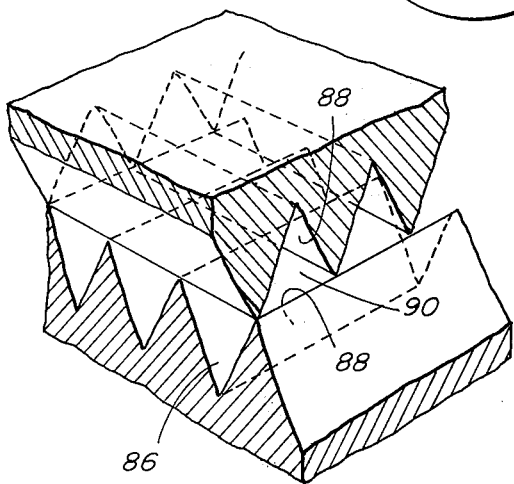
Figure 4:
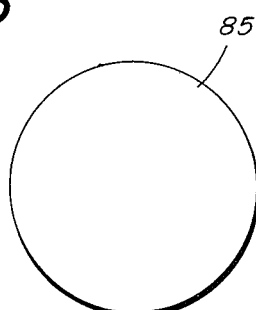
FIG. 4 is a side view of another product embodying the present invention.
Figure 4:
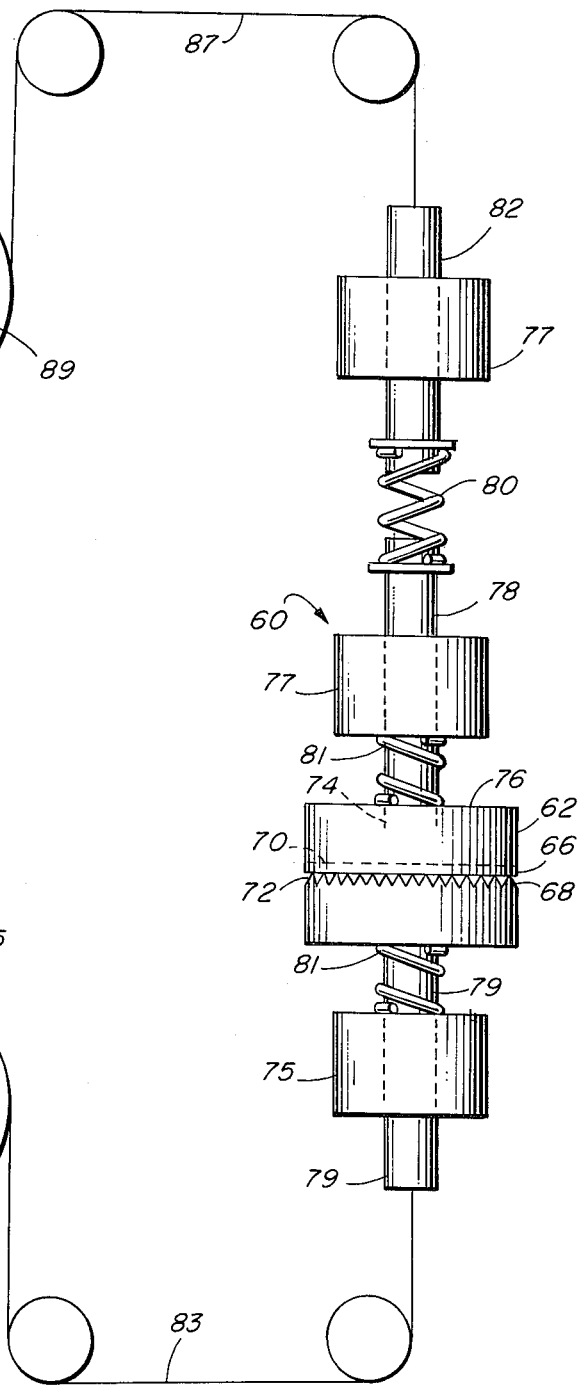

Referring now to the drawings, particularly FIGS. 4, 5 and 6, there is shown one embodiment of the invention in the form of a device 60 comprising a pair of separable cooperating members 62 and 64 having working faces 66 and 68, respectively. Members 62 and 64 are composed of a dimensionally stable material, for example a vitreous material such as glass, a plastic such as methyl methacrylate, or a metallic material such as stainless steel. Each working face defines a bearing surface of predetermined surface characteristics having troughs and ridges of triangular or other cross section, the average valley to peak height being in the range of 0.001 to 5.0 mm. Such a surface, in various embodiments, is characterized by a predetermined depth and is provided by precision casting, machining, hot pressing or etching regularly spaced troughs and ridges, the outermost area of the ridges being non-planar, i.e. being sharp or rounded. In cross section, these spaced valleys and peaks take the form of elongated increments which extend outwardly to ridge lines. In the illustrated embodiment, by way of example, the predetermined surface of bearing surface 6, which is disposed at the lower face of member 12, is in the form of a plurality of elongated members 70 that are in spaced parallel relationship with one another, each elongated member 70 having a triangular cross-section profile occurring at a rate of 5 to 5000 cycles per cm. In the illustrated embodiment, by way of example, the predetermined surface of bearing surface 68, which is disposed at the upper face of member 64, is in the form of a plurality of elongated members 72 that are in spaced parallel relationship with one another, each elongated member 72 having a triangular cross-sectional profile occurring at a rate of 5 to 5000 cycles per cm.

In accordance with the present invention, each of surfaces 66 and 68 are predeterminedly porous, being characterized by sufficient capillarity to absorb water and other aqueous, substantially Netwonian free-flowing fluids. Preferably the pore diameter should average in the range from 0.1 to 500 microns on the depth of the porous layer underlying the porous surface should be excess of 1 micron ranging normally up to 200 microns. In various forms, the porous bearing surfaces are provided by fired ceramic materials, etched vitreous materials (particularly glasses), sintered powder metallurgical composites, and etched metals and alloys. A particularly satisfactory material is produced by etching the copper out of aluminum bronze by an acid, particularly sulfuric acid.

Member 62, which in the illustrated embodiment has a circular (or square or rectangular) profile having a diameter in the range of 0.5 to 4.0 cm, is formed with an axial opening 74 at an upper face 76. One end of a rod 78 is pressed or threaded into opening 74, rod 78 projecting outwardly from and in perpendicular relationship with face 76. One end of a resilient element 80, for example a spring, is secured to the free end of rod 78. The other end of spring 80 is fastened to a rod 82, which is coaxial with rod 78. Rods 78 and 82 are composed of a suitable plastic such as methyl methacrylate or polycarbonate. Element 62, 64 are constrained for reciprocal motion toward and away from each other by a pair of slide bearings 75, 77, which receive rod 78 and a rod 79 extending from member 64 in the manner that rod 78 extends from member 62. In operation, elements 62, 64 initially are biased toward each other by springs 81, 81 with a fluid sample at the interface. Rod 79 is connected by a tension line 83 to a memory torque meter 85. Rod 87 is connected by a tension line 83 to a memory torque meter 85. Rod 82 is connected by a tension line 87 to a synchronous motor 89 having the characteristics of constant torque at constant or variable speed. The bias applied, typically ranges from 0.1 to 1000 grams and is related to the size and configuration of members 62 and 64. The profile of member 64 conforms substantially to the profile of member 62.

OPERATION OF THE EMBODIMENT OF FIGS. 4, 5 AND 6

One process of the present invention, hereinafter described, involves the use of device 60 for determining the properties of a fluid. First, a sample of fluid is obtained by inserting member 62 into the fluid or by placing a sample between the surfaces. Next, member 62 is removed from the fluid, a sample of fluid being contained on bearing surface 66. Next, immediately after removal of member 62, bearing surface 66 is placed on and pressed against bearing surface 68, whereby the fluid is spread on the bearing surfaces. Bearing surface 66 is placed on bearing surface 68 in such a manner that the longitudinal axis of each elongated member 70 is disposed in substantially perpendicular relationship with respect to the longitudinal axis of each elongated member 72. When members 62 and 64 are pressed together, a plurality of fluid containing regions 86 are formed therebetween. The surface area of each fluid containing regions is substantially greater than the surface area of the interface between the bearing surfaces, the surfaces of region 86 being denoted by reference character 88 and the interface being denoted by reference character 90. When the bearing surfaces are pessed together, the fluid sample is spread to the boundary surfaces of regions 86 and excess flows out of the extremities of the troughs, the bearing surfaces being operative to provide an even thickness of the spread fluid. Next, synchronous motor 89 pulls upwardly on tension line 87 or in a direction that is substantially perpendicular to the plane of the interface between members 62 and 64. The more viscous the fluid, the greater the force necessary to pull the elements apart. Spring 80 is operative to prevent shock loading during mating of the members 62 and 64 and during separation of the members.

It is to be understood that the present invention contemplates a variety of control techniques by which precise measurements of rheological properties can be obtained. It is to be understood that the present invention contemplates the use of eccentrically positioned ciruclar bearing surfaces as well as the concentric bearing surfaces specifically disclosed herein. Since certain changes may be made in the present disclosure without departing from the scope hereof, it is intended that all matter contained in the above specification or shown in the accompanying drawing be interpreted in an illustrative and not in a limiting sense.

What is claimed is:

1. A device for association with means for testing fluid samples, said device comprising a first bearing means and second bearing means, constrained for relative motion with respect to each other, at least one of said bearing means presenting a porous surface, and bias means tending to cause relative motion between said bearing means.

2. The device of claim 1 wherein said first bearing means and said second bearing means define a shear region, the axial length of said sheer region ranging between 0.3 and 5 centimeters.

3. The device of claim 1 wherein the radial distance between the inner and outer bearing means ranges between 0.0001 and 0.050 millimeters.

4. The device of claim 1 wherein the pore diameter of said porous surface averages between 0.1 and 500 microns.

5. Means for association with means for testing fluid samples; said first-mentioned means comprising a first bearing means and a second bearing means adapted for rotational motion with respect to each other, said first bearing means and said second bearing means presenting porous bearing surfaces, support means affixed to said first bearing means, and bias means affixed to said second bearing means.

6. The first-mentioned means of claim 5 wherein said first bearing means and said second bearing means define a shar region, the axial length of said shear region ranging between 0.3 and 5 centimeters.

7. The first-mentioned means of claim 5 wherein the radial distance between the inner and outer bearing means ranges between 0.0001 and 0.050 millimeters.

8. The first-mentioned means of claim 5 wherein the pore diameter of said porous surface averages between 0.1 and 500 microns.

9. A process for tesing a fluid sample having at least a high viscosity component and at least a low viscosity component, said process comprising the steps of interposing a fluid sample between a first bearing means and a second bearing means; at least one of said bearing means presenting a porous surface, absorbing said low viscosity component into said porous surface, biasing said first bearing means and said second bearing means with respect to each other, and means for indicating the relative motion of said first bearing means with respect to said second bearing means as an indication of the characteristics of said fluid sample.

10. The process of claim 9 wherein said first bearing means and said second bearing means define a shear region, the axial length of said shear region ranging between 0.3 and 5 centimeters.

11. The process of claim 9 wherein the radial distance between the inner and outer bearing means ranges between 0.0001 and 0.050 millimeters.

12. The process of claim 9 wherein the pore diameter of said porous surface averages between 0.1 and 500 microns.

13. A device for testing a fluid sample, said device comprising a first bearing means and a second bearing means, constrained for rotary motion with respect to each other, bias means tending to cause relative motion between said bearing means, said bearing means establishing a test region therebetween, said first bearing means and said second bearing means having contiguous porous surfaces, and means for indicating said rotary motion as a function of the characteristics of said fluid sample.

14. The device of claim 13 wherein said first bearing means and said second bearing means define a shear region, the axial length of said sheer region ranging between 0.3 and 5 centimeters.

15. The device of claim 13 wherein the radial distance between the inner and outer bearing means ranges between 0.0001 and 0.050 millimeters.

16. A device for testing biological samples, said device comprising a first bearing means and a second bearing means for reciprocal motion with respect to each other, said first bearing means comprising a plurality of parallel ridges and said second bearing means having a plurality of parallel ridges, said first bearing means and said second bearing means having contiguous porous surfaces, and means related to said motion for indicating the characteristics of said biological samples.

* * * * *